United States Patent [19]

Yamanaka

[11] Patent Number: 5,623,212

[45] Date of Patent: Apr. 22, 1997

[54] ODOR CONCENTRATION MEASUREMENT METHOD AND APPARATUS FOR USE IN FIRE DETECTION

[75] Inventor: Shigeo Yamanaka, Tokyo, Japan

[73] Assignee: Nohmi Bosai Ltd., Tokyo, Japan

[21] Appl. No.: 404,096

[22] Filed: Mar. 14, 1995

[30] Foreign Application Priority Data

Mar. 23, 1994 [JP] Japan ................................ 6-052214

[51] Int. Cl.⁶ .......................... G01R 27/08; G01N 27/04
[52] U.S. Cl. ............................................. 324/693; 422/83
[58] Field of Search ................................ 340/632–634, 340/628; 73/23.34, 23; 422/83, 88, 82.02; 324/691, 693, 705, 717

[56] References Cited

U.S. PATENT DOCUMENTS

4,770,027  9/1988  Ehara et al. ......................... 73/23.34
5,177,994  1/1993  Moruzumi et al. .................. 73/23.34

Primary Examiner—Sandra L. O'Shea
Assistant Examiner—Roger Phillips
Attorney, Agent, or Firm—Wenderoth, Lind & Ponack

[57] ABSTRACT

An odor concentration is measured by energizing an odor sensor connected across a power supply through a load resistance. A total resistance of the odor sensor is represented by and includes a parallel connection of a first resistive component having a value according to surrounding environmental conditions and a second resistive component having a value according to an odor concentration, and a saturation resistive component connected in series with the parallel connection of the first and second resistive components. A CPU is used to measure the odor concentration by obtaining the value of the second resistive component from an output of the odor sensor which is a voltage across the load resistance. Also, the measured odor concentration can be normalized and compared with a given threshold for fire detection.

14 Claims, 9 Drawing Sheets

ODOR CONCENTRATION MEASUREMENT METHOD AND APPARATUS FOR USE IN FIRE DETECTION

BACKGROUND OF THE INVENTION

1. Field of the Invention

This invention relates to the equivalent circuit of an environmental sensor, the resistance of which changes depending on the state of an object to be detected in the ambient atmosphere (that is, in an environment), namely, depending on, for example, a gas or an odor, like a gas sensor for detecting a gas generated when a fire occurs, for instance, a CO-gas and an odor sensor (namely, an odorant sensor) for detecting a smoky smell or odor when a fire brakes out. Further, this invention relates to a method for measuring an odor pressure, a method for normalizing an odor pressure, an odor detection system and a fire detection system.

2. Description of the Related Art

Figure 8:
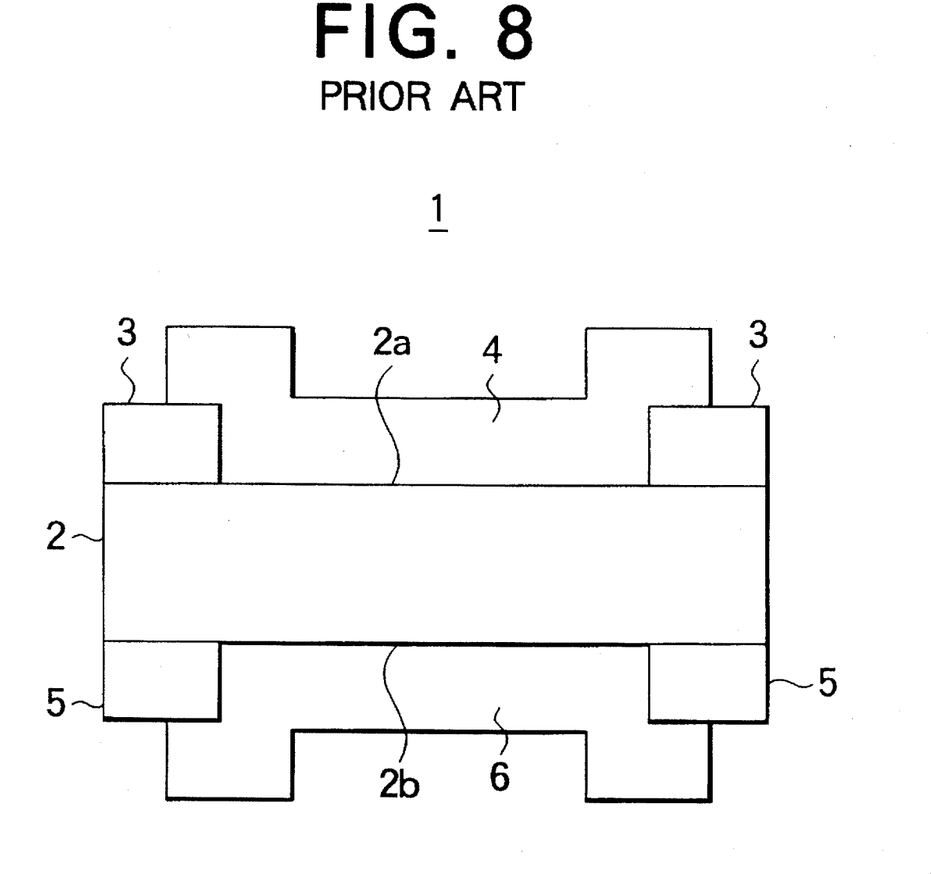
FIG. 8 is a sectional view of a conventional odor sensor serving as an environmental sensor.

There has been known a conventional environmental sensor for detecting the state of an odor pressure (i.e., the concentration or strength of an odor) in the environment thereof, which comprises a sensitive film, the resistance of which changes according to the variation in odor pressure (corresponding to an odor intensity, an odor quantity, a gas pressure or a gas concentration) of an object to be detected, and a heater for heating this sensitive film. FIG. 8 is a sectional view of a conventional environmental sensor, for example, a thin-film odor sensor. In this figure, reference numeral 1 designates the odor sensor which comprises an insulating substrate (for instance, an alumina substrate) 2, a sensor electrode 3 mounted on a surface, for example, the top surface 2a of this alumina substrate 2, a sensitive film 4 consisting of a metal oxide semiconductor (for example, $SnO_2$, $ZnO$, $TiO_2$ or the like) deposited or vapored on both of the top surface 2a of the alumna substrate 2 and the surface of the sensor electrode 3 and having resistance which changes according to the odor pressure, a heater electrode 5 mounted on another surface, for instance, the bottom surface 2b of the alumina substrate 2, and a thin film serving as a heater (for instance, a platinum thin film) 6 which is deposited on both of the bottom surface 2b of the alumina substrate 2 and the surface of the heater electrode 5. This platinum thin film 6 heats the sensitive film 4 through the alumina substrate 2. This promotes the change in resistance of the sensitive film 4 depending on the odor pressure, to thereby increase the sensitivity of the film 4.

The conventional odor sensor 1 is constituted as described above. However, there are two types of the sensitive films 4, namely, n-type and p-type films. In the case of the n-type of the sensitive film 4, when an odor pressure is exerted thereon, it accepts an electron to change its resistance. In contrast, in the case of the p-type of the sensitive film 4, when an odor pressure is exerted thereon, an electron is extracted from the sensitive film 4, with the result that the resistance thereof changes. Further, the odor sensor 1 is one for detecting an odor by utilizing the resistance change which depends on the odor pressure. It has been well known from, for example, a paper described by P. K. Clifford (see Proceeding of the International Meeting of Chemical Sensors, Fukuoka, Sept, 1983, A113) that the power law given by the following equation (1) can be generally applied to the odor-pressure-sensor-resistance characteristics.

$$Z=AP^{-a} \quad (1)$$

where Z represents a total resistance of the sensitive film 4 of the odor sensor 1; P an odor pressure; and A a proportional constant. Incidentally, an exponent "a" varies with odors and meets the following inequality: $0<a<1$.

As stated above, in the case of the conventional odor sensor, the exponent "a" varies with odors and is smaller than 1. Thus, the conventional odor sensor has drawbacks in that it is very difficult to treat a compound odor and in that it is impossible to measure a partial odor pressure of a specified odor in the compound odor whose composition is unknown.

The present invention is accomplished to eliminate such drawbacks of the conventional environmental sensor.

Accordingly, an object of the present invention is to provide a specified equivalent circuit of an environmental sensor which can eliminate the drawbacks of the conventional environmental sensor.

Further, another object of the present invention is to provide a method for measuring an odor pressure by obtaining and utilizing a resistance $r_n$ which changes on the basis of the odor pressure in such a manner that the exponent "a" becomes equal to 1.

Moreover, a further object of the present invention is to provide a method for normalizing the odor pressure.

Furthermore, still another object of the present invention is to provide an odor detection system which utilizes such methods.

Additionally, yet another object of the present invention is to provide a fire detection system which utilizes such methods.

SUMMARY OF THE INVENTION

To achieve the foregoing object, in accordance with a first aspect of the present invention, there is provided an equivalent circuit of an environmental sensor, which comprises a saturation resistance $r_0$, a first resistance $r_a$ being affected by an environment thereof and a second resistance $r_n$ adapted to change according to an odor pressure, wherein the saturation resistance $r_0$ is connected in series with a parallel connection of the first and second resistances $r_a$ and $r_n$.

Thus, this equivalent circuit has an effect or advantage in that the resistance $r_n$ can be easily obtained.

In accordance with a second aspect of the present invention, there is provided a method for measuring an odor pressure, which comprises the steps of obtaining a second resistance $r_n$ adapted to change according to an odor pressure by using an equivalent circuit of an environmental sensor having a saturation resistance $r_0$, a first resistance $r_a$ being affected by an environment thereof, and the second resistance $r_n$ in which the saturation resistance $r_0$ is connected in series with a parallel connection of the first and second resistances $r_a$ and $r_n$, and measuring the odor pressure from the obtained second resistance $r_n$.

Thus, this method has an effect in that the odor pressure can be easily measured from the resistance $r_n$.

In accordance with a third aspect of the present invention, there is provided an odor-pressure normalizing method including the step of obtaining a normalizing odor pressure N, which is used to normalize an odor pressure by using a second resistance $r_n$ adapted to change according to an odor pressure, from a reference resistance $r_{ns}$ corresponding to a reference odor pressure by $$N=r_{ns}/r_n.$$

Thus, this method has an effect in that the odor pressure detected by the environmental sensor can be easily normalized.

In accordance with a fourth aspect of the present invention, there is provided an odor detection system, which comprises an environmental sensor for detecting an odor pressure and a normalizing output portion connected to the environmental sensor. In this odor detection system, the normalizing output portion comprises a memory for storing a value of a load resistance R, a value of a voltage supplied from a power supply V, a saturation level $E_m$ of the environmental sensor, the base level $E_0$ of the environmental sensor and a reference resistance $r_{ns}$ therein, and a ROM for storing equations expressed as follows:

$$r_n = R \cdot V(E_m - E)(E_m - E_0)/E_m^2(E - E_0),$$
$$N = r_{ns}/r_n$$
$$= r_{ns} \cdot E_m^2(E - E_0)/R \cdot V(E_m - E)(E_m - E_0)$$

where $r_n$ is a resistance adapted to change according to an odor pressure. The normalizing output portion further comprises a CPU for calculating the normalizing odor pressure N from the output of the environmental sensor according to these equations.

Thus, this odor detection system has an effect in that a measured value being proportional to an odor pressure can be obtained by using an inexpensive environmental sensor. In this respect, a conventional odor detection system can be used for detecting the presence or absence of an odor but is unsuitable for a quantitative measurement of the odor owing to the variation in the base level dependent on an environment and the difficulty in measuring a partial odor pressure of a specified odor component of a compound odor. However, in the case of the odor detection system of the present invention, the quantitative measurement of an odor can be performed. Whereby, the present invention has an effect in that an inexpensive odor detection system can be provided in many technical fields such as those of pollution measurement, air-conditioning, foods and perfumes.

In accordance with a fifth aspect of the present invention, there is provided an odor detection system which comprises an environmental sensor for detecting an odor pressure and a normalizing output portion connected to the environmental sensor. In this odor detection system, the normalizing output portion comprises a memory for storing a reference resistance $r_{ns}$, a value $Z_n$ of the total resistance at the time when an odor pressure is measured by the environmental sensor, a value $Z_m$ of a total resistance of the environmental sensor at the time when the output of the environmental sensor is saturated, and a value $Z_0$ of the total resistance at the time when the output of the environmental sensor has the base level therein, and a ROM for storing equations expressed as follows:

$$r_n = (Z_n - Z_m)(Z_0 - Z_m)/(Z_0 - Z_n)$$
$$N = r_{ns}/r_n$$
$$= r_{ns}(Z_0 - Z_n)/(Z_n - Z_m)(Z_0 - Z_m)$$

where N and $r_n$ are a normalizing odor pressure and a resistance adapted to change according to an odor pressure, respectively. The normalizing output portion further comprises a CPU for calculating the normalizing odor pressure from the output of the environmental sensor according to the equations.

Thus, this odor detection system has effects in that when measuring parameters, neither the load resistance R nor the voltage V affects a result of the calculation and that this odor detection system is of great practical value, in addition to the effect of the odor detection system of the fourth aspect of the present invention.

In accordance with a sixth aspect of the present invention, there is provided a fire detection system which comprises an environmental sensor for detecting an odor pressure, a normalizing output portion of the fourth or fifth aspect of the present invention and a fire judgment portion, connected to the normalizing output portion, for judging on the basis of data representing the normalizing odor pressure output from the normalizing output portion whether or not a fire occurs.

Thus, a smoldering phase of a fire can be detected at an extremely early state by using the quantitative measurement of an odor pressure, in comparison with a conventional fire detection system. In this regard, the conventional fire detection system detects a fire from a smoke or heat. In contrast, the fire detection system of the present invention can detect an odor pressure prior to a smoking phase of a fire. Consequently, the fire detection system of the present invention has an effect in that a fire can be detected at an extremely early stage.

BRIEF DESCRIPTION OF THE DRAWINGS

Other features, objects and advantages of the present invention will become apparent from the following description of preferred embodiments with reference to the drawings in which like reference characters designate like parts throughout several views, and in which.

DETAILED DESCRIPTION OF THE PREFERRED EMBODIMENTS

Hereinafter, the preferred embodiments of the present invention will be described in detail by referring to the accompanying drawings.

Although the base level of an output of the odor sensor 1, which is obtained when the odor pressure, namely, the (partial) pressure of an odor to be detected by the sensor is 0, largely changes depending on the environment, the saturation level thereof is nearly constant irrespective of the environment. Incidentally, even when the odor pressure to be detected is 0, an additional odor other than the odor to be detected is present in a normal environment. This additional odor causes the base level to vary. More particularly, it is apparent from the results of experiments, which are shown in FIG. 3, that the saturation levels of sensor outputs corresponding to a predetermined odor pressure are close to one another regardless of the base level, that the higher the odor pressure becomes, the closer the saturation levels come to and that finally, the saturation levels become nearly equal to one another. This results in assuming the equivalent circuit of FIG. 1.

Figure 1:
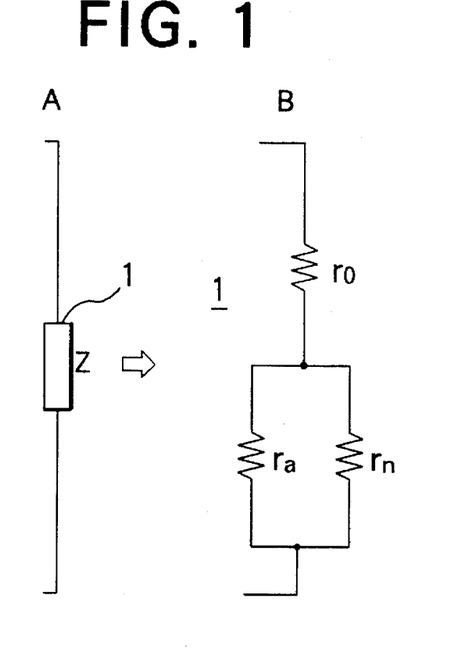
FIG. 1 is a circuit diagram for illustrating the equivalent circuit of an odor sensor according to the present invention.

In FIG. 1, reference character Z represents the total resistance of the odor sensor 1; $r_0$ the saturation resistance of the odor sensor 1, whose value is inherent in the sensor 1; $r_a$ a resistance which is affected by the environment, for example, temperature, humidity and odors other than the odor of an object to be detected; and $r_n$ a resistance which changes according to the state of the odor of an object to be detected, for instance, according to the odor pressure. The total resistance Z is equivalent to the resistance of the equivalent circuit in which $r_0$ is connected in series to a parallel connection of the resistances $r_a$ and $r_n$. If the resistance $r_n$ changes from infinity to 0, the total resistance Z is equivalent only to the resistance $r_0$ when the output of the sensor is saturated. Further, when the odor pressure is 0, the resistance $r_n$ is infinity and the total resistance Z is equal to the sum of the resistances $r_0$ and $r_a$. Thus the total resistance Z comes to change depending only on the environment. Consequently, this is in agreement with a phenomenon observed during the experiments.

Therefore, the resistance $r_n$ can be calculated backward from the sensor output by finding the resistance $r_0$ from the saturation level by use of the equivalent circuit of FIG. 1 and further finding the resistance $r_a$ from the base level at the time when the odor pressure is 0.

Figure 2:
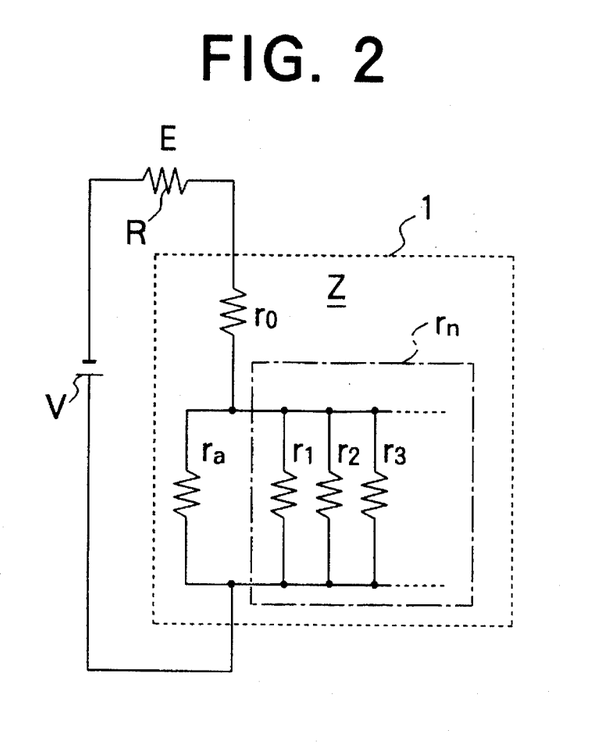
FIG. 2 is a circuit diagram for illustrating the configuration of a practical measurement circuit using an odor sensor according to the present invention.

A practical circuit is configured by connecting the odor sensor 1, the total resistance of which is Z as described above, to both terminals of a power supply V through a load resistance R as illustrated in FIG. 2. Further, a voltage E developed across both terminals of the load resistance R is taken as an output of the sensor 1. Therefore, the output E is given by the following equations (2) and (2').

$$E = R \cdot V/(R+Z) \qquad (2)$$
$$= R \cdot V/[R+r_0+r_n/(r_a+r_n)] \qquad (2')$$

Here, let $E_m$ and $E_0$ denote the saturation level of outputs of the odor sensor 1 and the base level thereof, respectively. These levels are given by the following equations (3) and (4).

$$E_m = R \cdot V/(R+r_0) \qquad (3)$$

$$E_0 = R \cdot V/(R+r_0+r_a) \qquad (4)$$

On the other hand, setting $r_a \cdot r_n/(r_a+r_n)=r'$, the following equation (5) is obtained:

$$r_n = r' \cdot r_a/(r_a-r') \qquad (5)$$

Further, the following equation (6) is obtained from the equation (2'):

$$r' = R \cdot V/E - R - r_0 \qquad (6)$$

Moreover, the following equation (7) is obtained from the equation (4):

$$r_a = R \cdot V/E_0 - R - r_0 \qquad (7)$$

Next, the substitution of the equations (3), (6) and (7) into the equation (5) gives the following equation (8):

$$r_n = R \cdot V(1/E - 1/E_m)(1/E_0 - 1/E_m)/(1/E_0 - 1/E) \qquad (8)$$
$$= R \cdot V(E_m - E)(E_m - E_0)/E_m^2(E - E_0)$$

Thus, if the saturation level $E_m$ and the base level $E_0$ of the odor sensor 1 and the load resistance R and the voltage supplied from the power supply V are known, the resistance $r_n$ varying on the basis of the odor pressure can be calculated from the output E of the odor sensor 1 by using the equation (8).

Further, the odor pressure n is in inverse proportion to the resistance $r_n$ and is thus given by the following equation (9)

$$n = B/r_n \qquad (9)$$

where B is a constant.

Moreover, a normalizing odor pressure N for normalizing the resistance $r_n$ by using a reference resistance $r_{ns}$ corresponding to a reference odor pressure is given by the following equation (10).

$$N = r_{ns}/r_n \qquad (10)$$
$$= r_{ns} \cdot E_m^2(E - E_0)/R \cdot V(E_m - E)(E_m - E_0)$$

Thus, if the saturation level $E_m$ and the base level $E_0$ of the odor sensor 1 and the load resistance R, the voltage supplied from the power supply V and the reference resistance $r_{ns}$ are known, the normalizing odor pressure N can be calculated from the output E of the odor sensor 1 by using the equation (10). Namely, when the normalizing odor pressure N is 1 (see FIG. 4B), the detected odor pressure is equal to the reference odor pressure. Further, if the normalizing odor pressure N is, for example, 0.5, the detected odor pressure is equal to half of the reference odor pressure.

Furthermore, let $Z_m$, $Z_0$ and $Z_n$ represent the value of the total resistance Z of the odor sensor 1 at the time when the output of the odor sensor 1 is saturated, that of the resistance Z at the time when the output of the sensor 1 has the base level, and that of the resistance Z at the time when the odor is measured by the sensor 1, respectively. Then, the normalizing odor pressure N is given by the following equation (11):

$$N = r_{ns}/r_n \qquad (11)$$
$$= r_{ns}(Z_0 - Z_n)/(Z_n - Z_m)(Z_0 - Z_m)$$

Incidentally, either a set of $E_m$ and $E_0$ or a set of $Z_m$ and $Z_0$ may be employed as a set of parameters being inherent in the sensor, which are used in calculating the normalizing odor pressure N. However, in view of the regardlessness of the load resistance R and the power supply M, the equation (11) is more popularly used.

Referring next to FIGS. 3A to 3D and 4A to 4D, there are shown raw data output from the sensor and normalizing odor pressures, which are obtained correspondingly to a constant odor pressure in different environments, respectively. FIGS. 3A, 3B, 3C and 3D show raw data obtained by burning sheets of copying paper in dry air (as indicated by dashed lines) and raw data obtained by burning the sheets of copying paper in air scented with the aroma of coffee (as indicated by dash-and-dot lines) and correspond to the sizes of the sheets of copying papers, which are 1 by 1 mm square, 2 by 2 mm square, 3 by 3 mm square and 5 by 5 mm square, respectively. Incidentally, each of FIGS. 4A, 4B, 4C and 4D shows the normalizing odor pressures obtained from the equation (10) or (11) by using the odor pressure found at the time of burning copying paper 2 by 2 mm square as the reference odor pressure and also using $r_n$ calculated from the equation (8) based on the raw data of the corresponding one of FIGS. 3A, 3B, 3C and 3D.

Figure 3A:
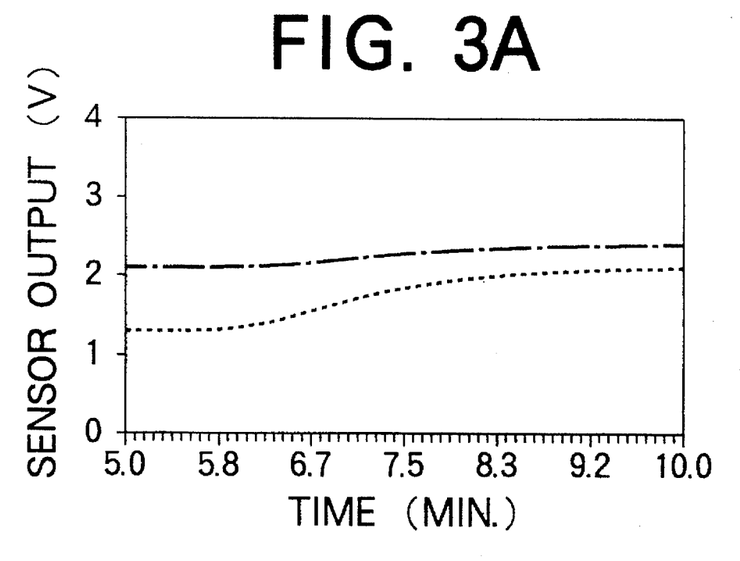
FIGS. 3A to 3D are graphs respectively illustrating raw data output from the sensor according to the present invention correspondingly to a given odor pressure in different environments.
Figure 3B:
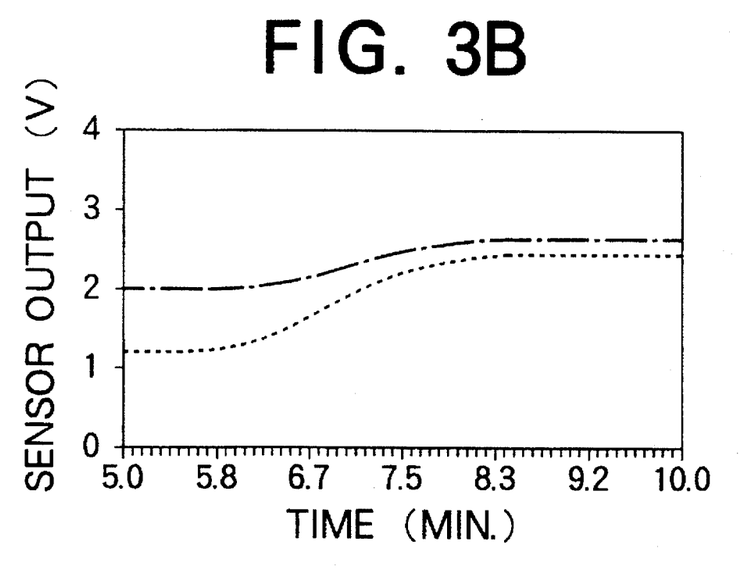
Figure 3C:
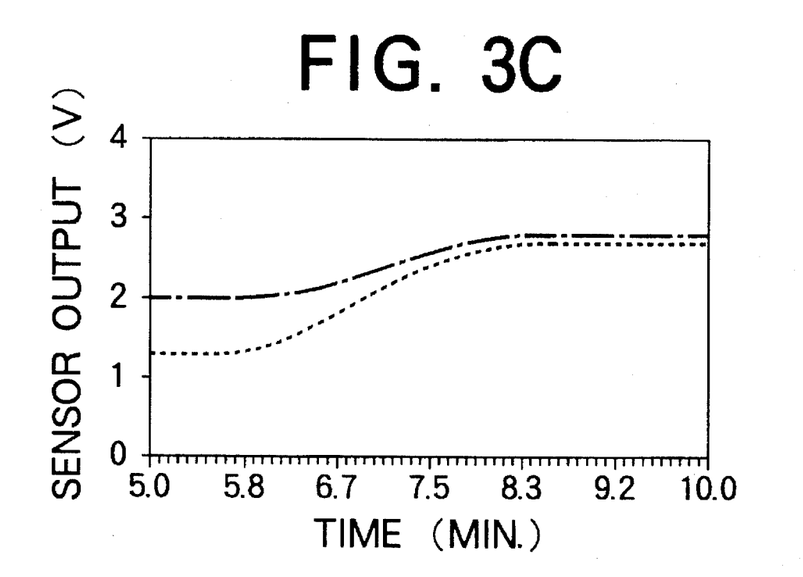
Figure 3D:
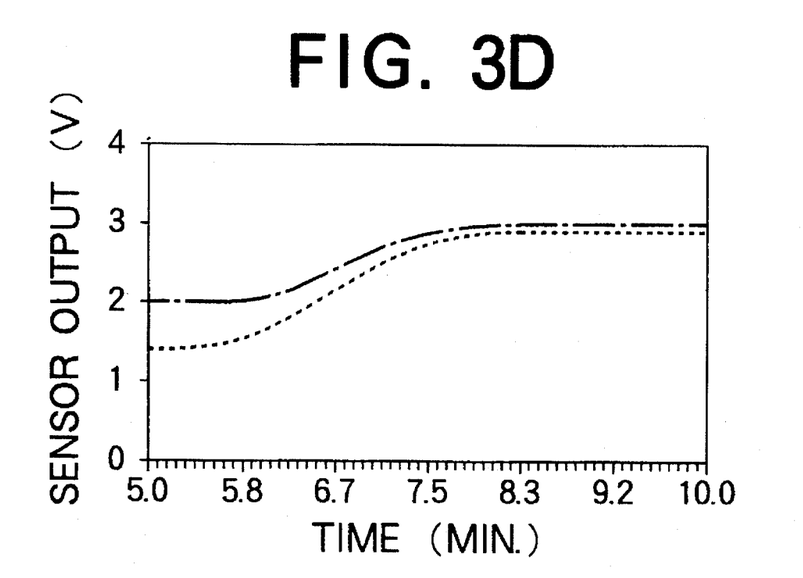
Figure 4A:
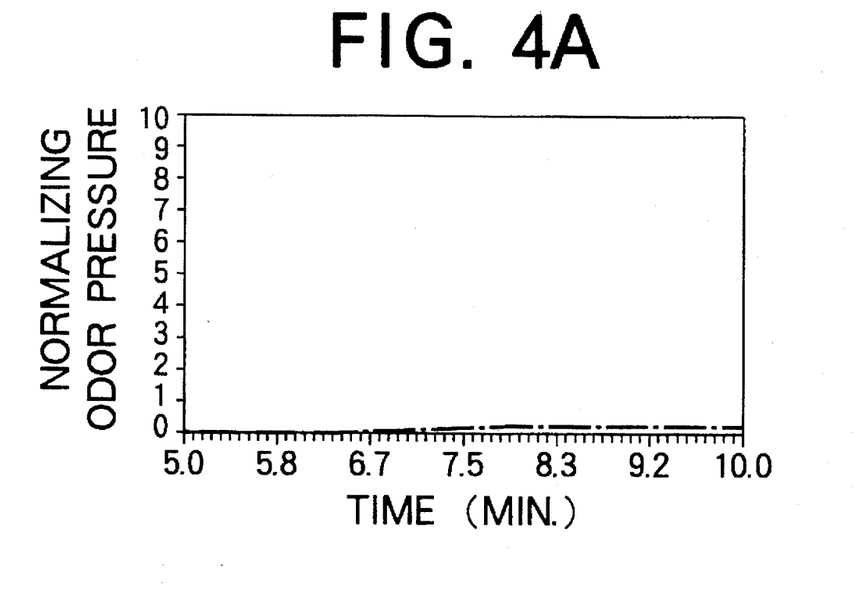
FIGS. 4A to 4D are graphs for illustrating normalizing odor pressures of the odor sensor according to the present invention.
Figure 4B:
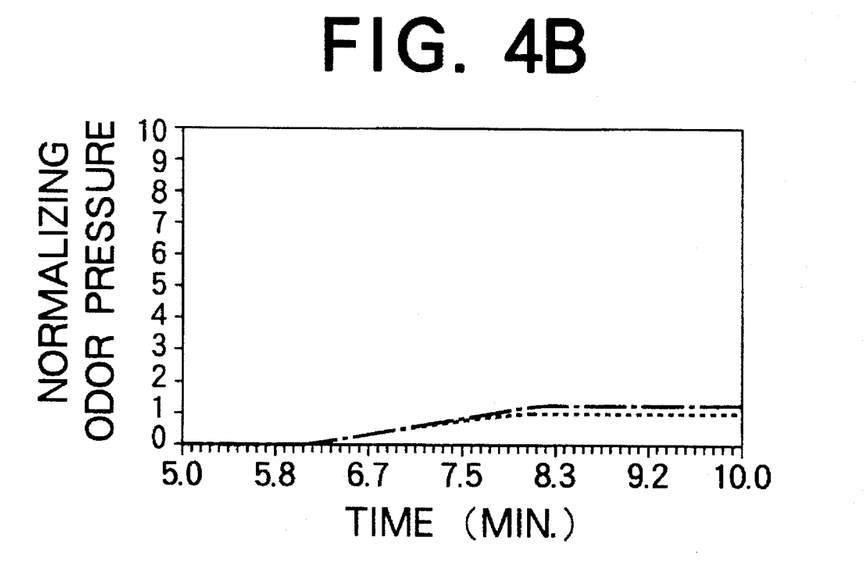
Figure 4C:
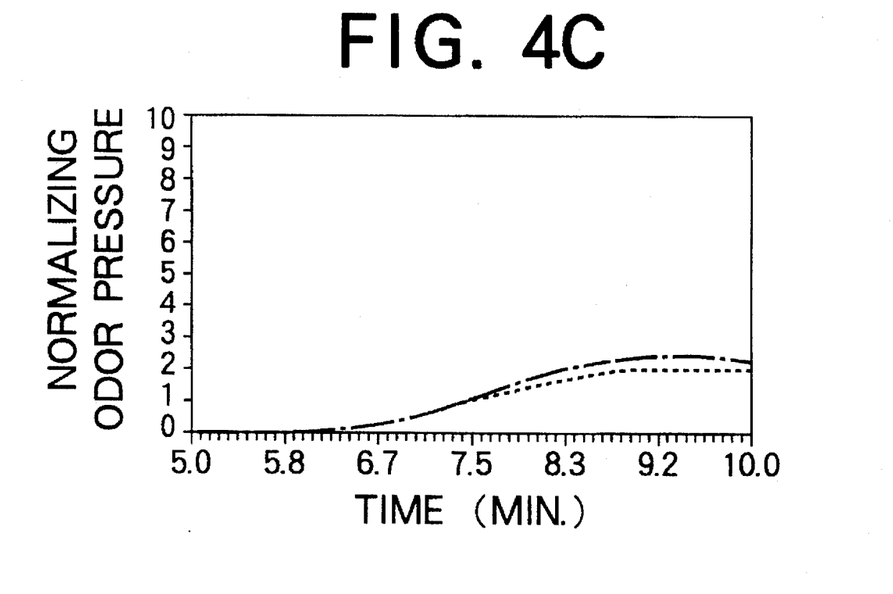
Figure 4D:
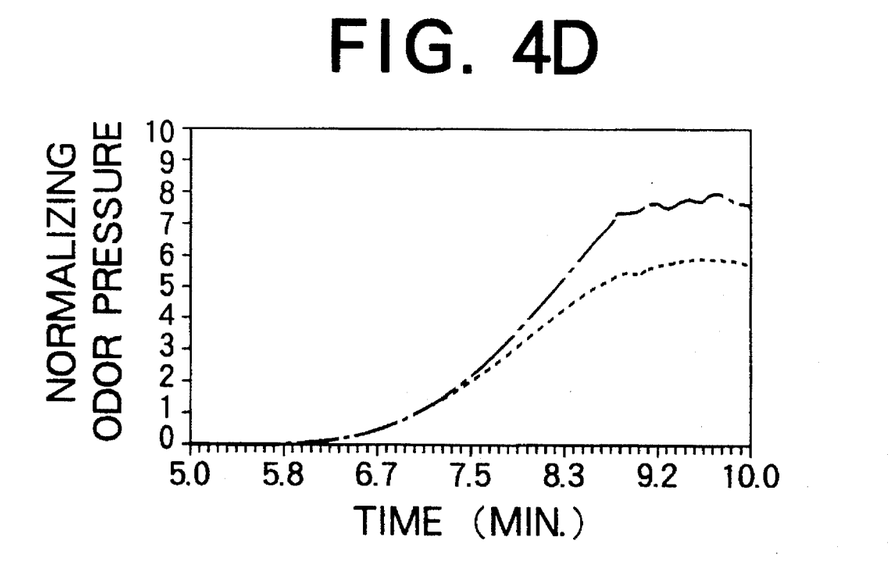

Hereinafter, the cases of FIGS. 3B and 4B will be described by way of example. As is seen from FIG. 3B, the base levels of the raw data of the sensor outputs respectively corresponding to the dry air and the air scented with the aroma of coffee are about 1.3 V and about 2.0 V and thus are rather different from each other. Moreover, the saturation levels thereof are about 2.5 V and about 2.7 V and thus there is a variation therebetween. In contrast, as shown in FIG. 4B, the levels obtained as a result of normalizing these sensor outputs are substantially the same, namely, almost 1.0 correspondingly to the same odor pressure, regardless of the atmosphere (namely, which of the dry air and the air scented with the aroma of coffee is selected). Even when the odor pressure is not constant but varies with time, the resultant levels are nearly in proportion to the odor pressure in all of the cases of FIGS. 4A to 4D except that there is a little variation in the levels, which are close to the saturation levels, in the case of FIG. 4D.

It is experimentally verified that in the case of the equivalent circuit of FIG. 1, the odor pressure P is nearly in inverse proportion to the resistance $r_n$ which varies depending on the odor pressure P. Thus, based on such an inversely proportional relation therebetween, the following equation becomes valid.

$$r_n = C/P \qquad (12)$$

where C is a proportional constant.

In the case of a mixture of more than one kinds of odors, the total odor pressure P is given by $$P = P_1 + P_2 + P_3 + \ldots \qquad (13)$$

where $P_1$, $P_2$ and $P_3$ denote partial odor pressures of the odors. Further, the substitution of the equation (13) into the equation (12) gives the following equation (14):

$$r_n = C/(P_1 + P_2 + P_3 + \ldots) \qquad (14)$$

Dividing both of the denominator and the numerator of the right side of the equation (14) by the constant C, the following equation (15) is obtained.

$$r_n = 1/(P_1/C + P_2/C + P_3/C \ldots) \qquad (15)$$

Here, the equation (15) can be rewritten as follows by setting $C/P_1 = r_1$, $C/P_2 = r_2$, $C/P_3 = r_3$, ...

$$r_n = 1/(1/r_1 + 1/r_2 + 1/r_3 \ldots) \qquad (16)$$

Apparently from the equation (16), the resistance $r_n$ consists of parallel-connected resistances $r_1, r_2, r_3 \ldots$, each of which is in inverse proportion to the partial odor pressure of the corresponding odor. Therefore, the variable resistance of the mixed odors can be represented by the parallel combination of equivalent resistances $r_1, r_2, r_3 \ldots$, each of which is in inverse proportion to the partial odor pressure of the corresponding odor, as illustrated in FIG. 2. Consequently, addition and subtraction can be easily performed on resistances $r_i$ respectively corresponding to odors. Moreover, it comes to be able to measure a specified odor pressure. For example, in the case of an odor pressure with its initial level being 0, only the odor pressure of an odorant to be detected can be measured by performing a zero-adjustment, at the time of starting a measurement in order to cancel the influence of all of the odors other than the odor to be detected.

Figure 5:
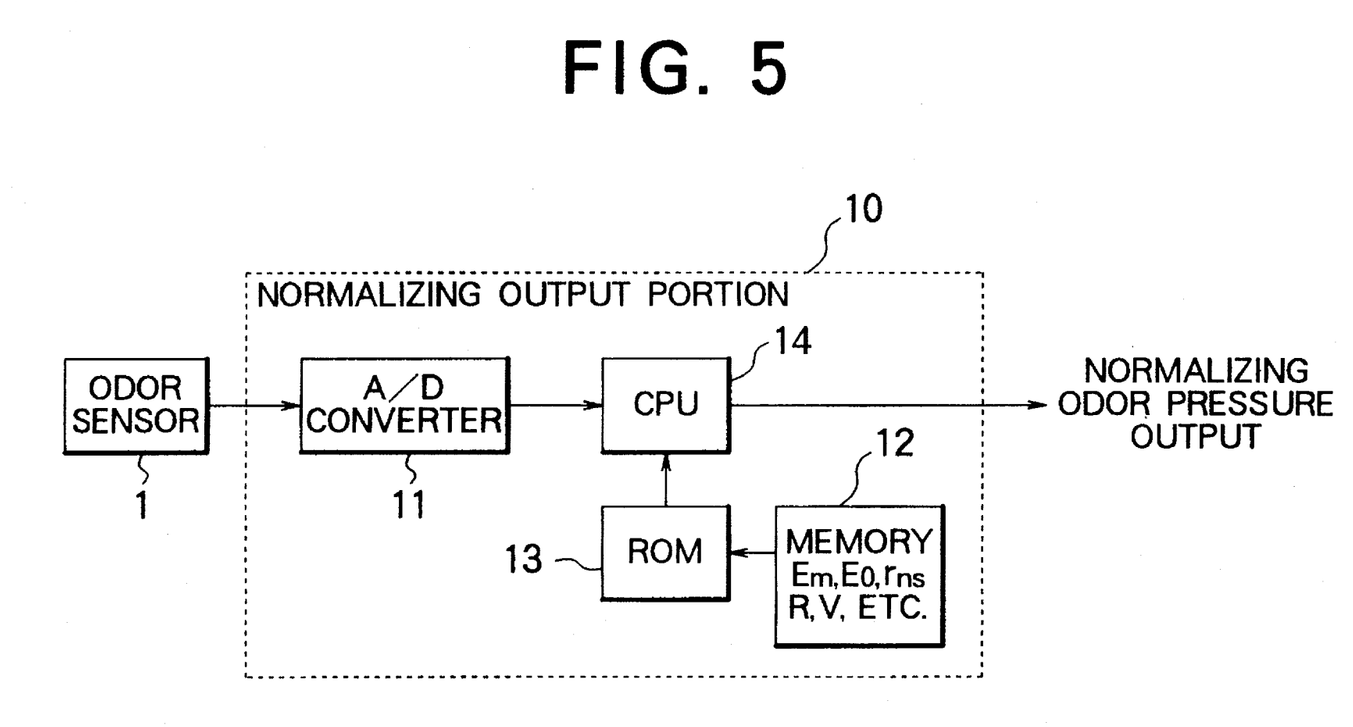
FIG. 5 is a block diagram for illustrating the configuration of an odor detection system according to the present invention.

FIG. 5 is a block diagram for illustrating the configuration of an odor detection system according to the present invention. In this figure, reference numeral 1 designates an odor sensor which is connected to a normalizing output portion 10. This normalizing output portion 10 comprises an analog-to-digital (A/D) converter 11 for converting an analog output of the odor sensor 1 into a digital output, a memory 12 for storing the saturation level $E_m$, the base level $E_0$, a reference resistance $r_{ns}$, the value of the load resistance R, the value of the voltage supplied from the power supply V and the values $Z_n$, $Z_m$ and $Z_0$ therein, a read-only memory (ROM) 13, connected to the memory 12, for storing data representing the equations (8) and (10) or (11) and a central processing unit (CPU) 14, connected to the A/D converter 11 and the ROM 13, for calculating a normalizing odor pressure N from a digital converted output of the odor sensor 1 and outputting the calculated normalizing odor pressure N, which is constituted by a one-chip microcomputer.

Figure 6:
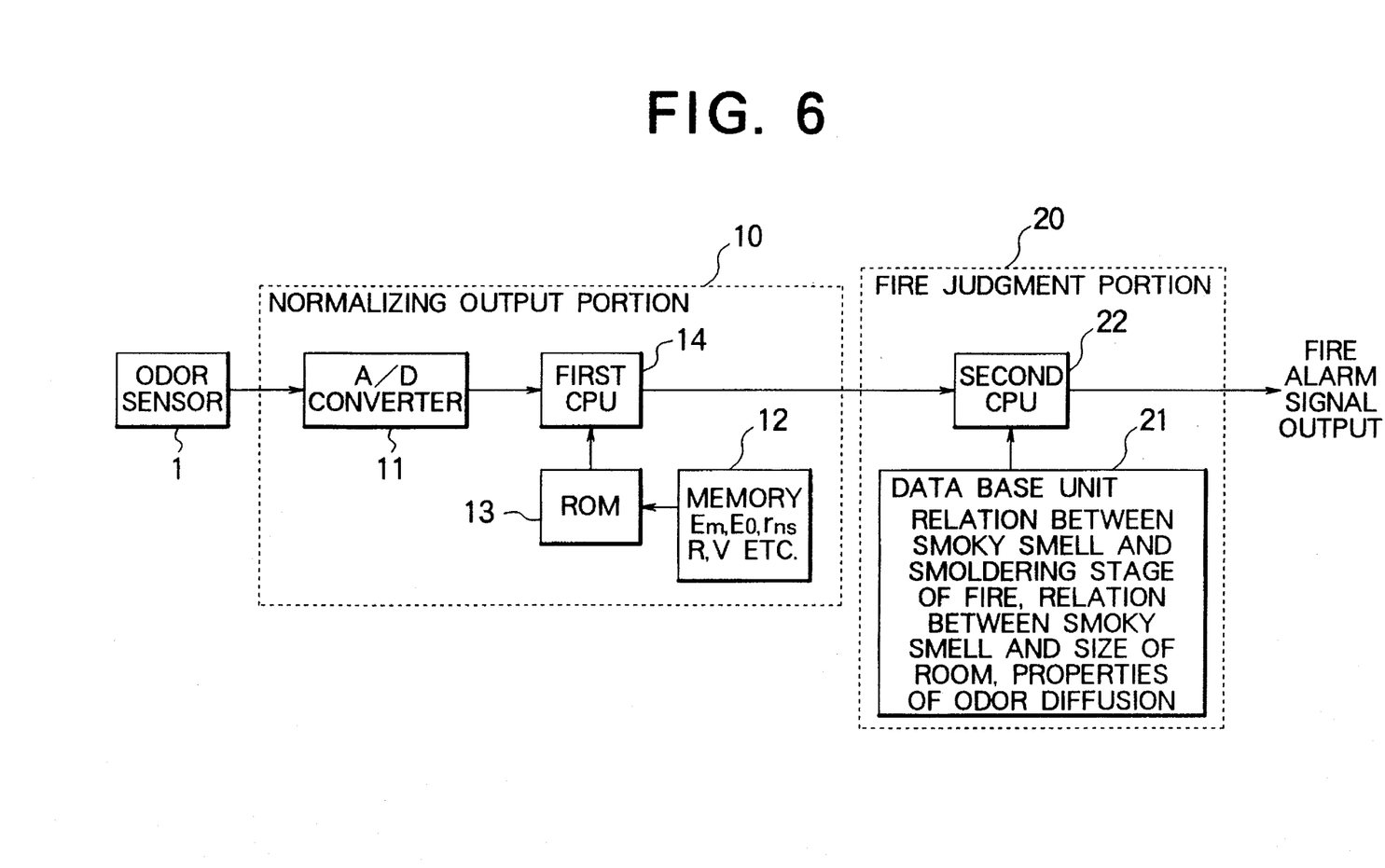
FIG. 6 is a block diagram for illustrating the configuration of a fire detection system according to the present invention.

FIG. 6 is a block diagram for illustrating the configuration of a fire detection system according to the present invention. In this figure, reference numerals 1 and 10 designate like components of FIG. 5. Incidentally, the CPU 14 will be referred to as a first CPU hereunder. Further, a fire judgment portion 20 connected to the normalizing output portion 10 comprisess a data base unit 21, which contains a ROM or an electrically erasable programmable read-only memory (EEPROM) for storing data representing the relation between the strength or intensity of a smoky smell and the smoldering stage of a fire, the relation between the size of a room, where the odor sensor 1 is provided, and the smoky smell and the properties of odor diffusion and the like, and a second CPU 22 connected to the first CPU 14 and the data base 21, which estimates the probability of occurrence of a fire, based on data representing the normalizing odor pressure N sent from the first CPU 14 and the data read from the data base unit 21 and outputs a fire alarm signal when the probability of occurrence of a fire is equal to or more than 60%.

Incidentally, in the case of this embodiment, the odor sensor 1, the normalizing output portion 10 and the fire judgment portion 20 may constitute a fire detector. In this case, a single CPU may be used in common by the normalizing output portion 10 and the fire judgment portion 20. The fire judgment portion 20 outputs a fire alarm signal to a receiving portion (not shown) of a fire control panel, or of a fire transmitter or the like.

Further, the fire detector may be constituted only by the odor sensor 1, or by the combination of the odor sensor 1 and the normalizing output portion 10. Moreover, the fire judgment portion 20 or the combination of the normalizing output portion 10 and the fire judgment portion 20 may be provided in the receiving portion. In this case, the fire detector may be provided with a transmitting/receiving circuit for converting an output of the odor sensor 1 or a normalizing odor pressure N output from the normalizing output portion 10 into a transmission signal such as a digital code when receiving, for instance, a polling signal from the receiving portion, and for outputting the transmission signal to the receiving portion.

Furthermore, a unit for judging in accordance with another fire judging method whether or not a fire occurs, for example, a unit for preliminarily storing a predetermined threshold value to be used to judge whether or not a fire occurs and for comparing a normalizing odor pressure N output from the normalizing output portion 10 with the predetermined threshold value to judge whether or not a fire occurs may be employed as the fire judgment portion 20.

Figure 7:
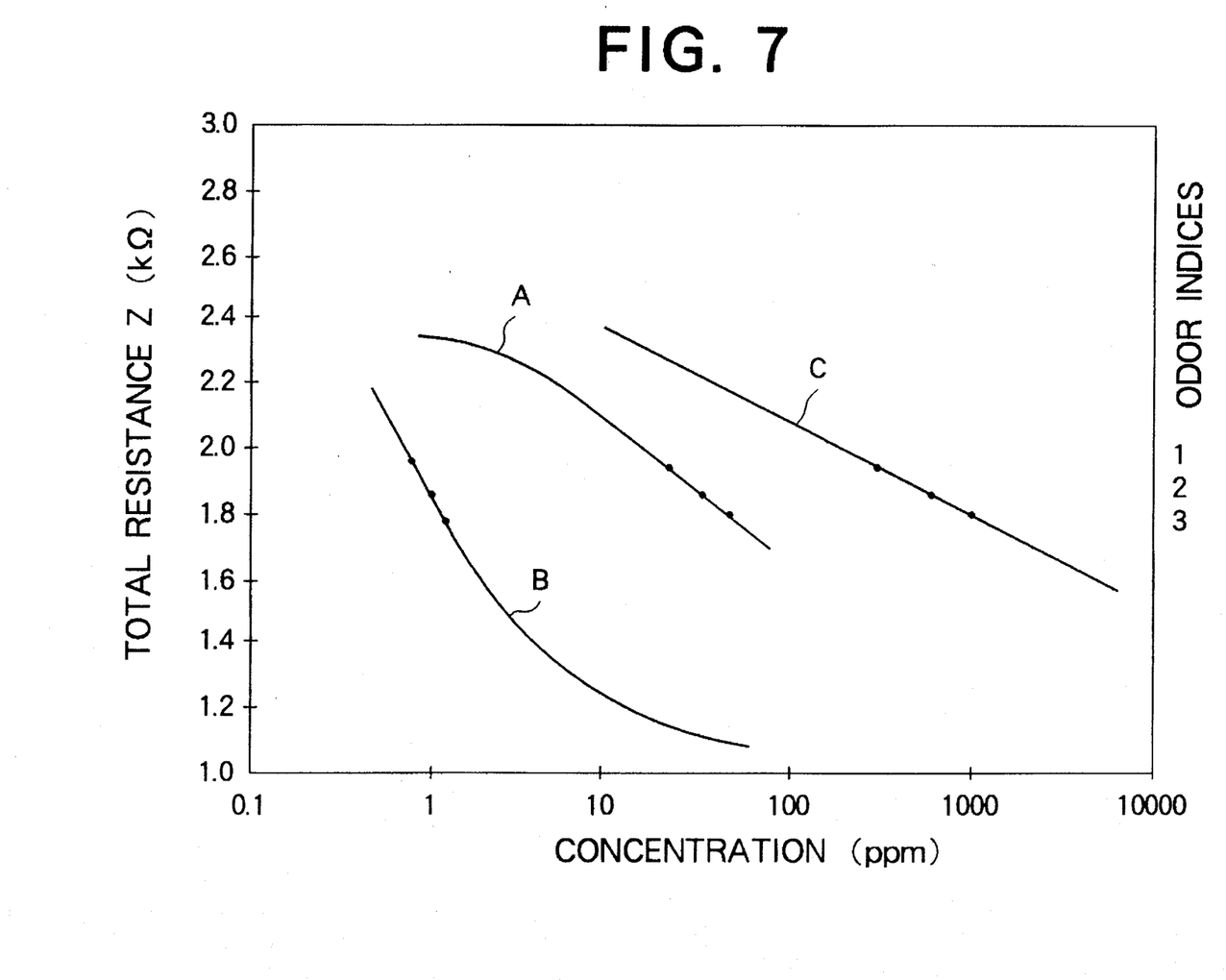
FIG. 7 is a graph for illustrating how an odor strength is converted into an odor index according to the present invention.

In the cases of the embodiments of the present invention, an odorant generated when a sheet of copying paper 5 by 5 mm square (corresponding to a curve A of FIG. 7) is burnt in a chamber having a capacity of 15 lit., namely, a smoky smell is used as a reference odorant. Further, as illustrated in FIG. 7, odor indices respectively corresponding to the values (namely, 1.95 KΩ, 1.85 KΩ and 1.8 KΩ) of the total resistance Z of the copying paper (A) are determined as 1, 2 and 3 (incidentally, the corresponding odor pressures (namely, the odor strengths) are 18 ppm, 20 ppm and 30 ppm). Next, Odors being present in the environment, for example, nicotine (corresponding to a curve B of FIG. 7) and ethanol (corresponding to a line C of FIG. 7) are detected by the odor sensor 1. Further, the odor strengths of these odorants are converted into odor indices at the same values of the total resistance as in the case of the copying paper (incidentally, as is apparent from FIG. 7, the odor strengths being on the curves A and B and the line C correspondingly to a value of the total resistance are different from one another).

In the odor detection system of FIG. 5, in place of the normalizing output portion 10, an odor digitizing portion having the same configuration as that of the portion 10 may be employed. Further, a display device (not shown) may be connected to an output terminal of the CPU for calculating the normalizing odor strength from the detected output of the odor sensor 1 and converting the odor strength into the odor index as above described with reference to FIG. 7. Whreby, the odor being present in the environment can be displayed in numerical representation.

In this manner, in accordance with the preseeent invention, an odor being present in the environment can be displayed in numerical representation as an odor strength obtained by a comparison with the smoky smell of copying paper which is employed as the reference odorant. Thus, the presence of an odor can be displayed in a representation which is easily perceived by human senses. Further, because the smoky smell of copying paper is used as a reference substance producing an odor, namely, as a reference odorant, a useful odor strength for judging whether or not a fire occurs can be found.

For the aforementioned reasons, a reference odorant may be selected according to both of an odor to be detected and a place where the sensor or detector is installed. For example, in the bases of detecting an odor being present in a toilet and a smell of a putrefied food, nitrogen-containing compounds, for instance, amines such as ammonia and trimethylamine, mercaptans such as a methylmercaptan and sulfur-containing compounds may be used as the reference odorant. Moreover, in the case of providing the sensor in a spa, hydrogen sulfide, sulfur dioxide or the like may be used as the reference odorant. In the case of using the sensor in the brewing industry, alcohol, for instance, ethanol may be used as the reference odorant. Additionally, in general, aromatics, for example, acrolein, acetone, ozone, nitrogen dioxide and benzene or the like and offensive odors may be employed as the reference odorant.

Further, the names of exemplary substances which can be employed as the reference odorant will be listed hereinbelow.

I. Sulfur-containing Compound
  [1] Inorganic Compound
    (1) Hydrogen Sulfide
  [2] Organic Compound
    (1) Mercaptan
      1) Methylmercaptan
      2) Ethylmercaptan
  (2) Sulfides
    1) Dimethyl Sulfide
    2) Diethyl Sulfide
II. Nitrogen-Containing Compound
  [1] Inorganic Compound
    (1) Ammonia
  [2] Organic Compound
    (1) Amine
      1) Methylamine
      2) Ethylamine
      3) Trimethylamine
III. Hydrocarbon
  [1] Organic Compound
    (1) Butylene
  Incidentally, there are four kinds of isomers.
IV. Oxygen-Containing Compound
  [1] Organic Compound
    (1) Aliphatic Unsaturated Aldehyde
      1) Acrolein
    (2) Aliphatic Ketone
      1) Acetone
    (3) Lower Aliphatic Carboxylic Acids
      1) Butyric Acid
  Incidentally, there are two kinds of isomers.

Although the preferred embodiments of the present invention have been described above, it should be understood that the present invention is not limited thereto and that other modifications will be apparent to those skilled in the art without departing from the spirit of the invention.

The scope of the present invention, therefore, is to be determined solely by the appended claims.

What is claimed is:

1. An odor concentration measurement method comprising the steps of:

energizing an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components; and measuring the odor concentration by obtaining the value of said second resistive component from an output E of said odor sensor which is a voltage across said load resistance, in accordance with $$rn = R \cdot V(Em-E)(Em-Eo)/Em^2(E-Eo)$$

where rn is the value of said second resistive component, R is a value of said load resistance, V is a value of a voltage supplied from said power supply, Em is a saturation level of the output of said odor sensor when the output is saturated, and Eo is a base level of the output of said odor sensor when there is zero odor concentration.

2. An odor concentration measurement method comprising the steps of:

energizing an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components;

obtaining the value of said second resistive component from an output E of said odor sensor which is a voltage across said load resistance, in accordance with $$rn = R \cdot V(Em-E)(Em-Eo)/Em^2(E-Eo)$$

where rn is the value of said second resistive component, R is a value of said load resistance, V is a value of a voltage supplied from said power supply, Em is a saturation level of the output of said odor sensor when the output is saturated, and Eo is a base level of the output of said odor sensor when there is zero odor concentration; and measuring a normalized odor concentration N from the value of said second resistance and a value of a reference resistance corresponding to a reference odor concentration, in accordance with $$N = rns/rn$$

where rns is the value of said reference resistance.

3. A method as claimed in claim 2, further comprising judging the presence or absence of a fire by comparing the normalized odor concentration N with a given threshold value.

4. An odor concentration measurement method comprising the steps of:

energizing an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components; and measuring the odor concentration by obtaining the value of said second resistive component from the total resistance of said odor sensor, in accordance with $$rn = (Zn-Zm)(Zo-Zm)/(Zo-Zn)$$

where rn is the value of the second resistive component, and where Zm, Zo and Zn are a value of the total resistance of said odor sensor when the output of said odor sensor is saturated, a value of the total resistance when the output of said odor sensor is at a base level, and a value of the total resistance when the odor concentration is measured by said odor sensor, respectively.

5. An odor concentration measurement method comprising the steps of:

energizing an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of the first and second resistive components;

obtaining the value of said second resistive component from the total resistance of said odor sensor, in accordance with $$rn = (Zn-Zm)(Zo-Zm)/(Zo-Zn)$$

where rn is the value of the second resistive component, and where Zm, Zo and Zn are a value of the total resistance of said odor sensor when the output of said odor sensor is saturated, a value of the total resistance when the output of said odor sensor is at a base level, and a value of the total resistance when the odor concentration is measured by said odor sensor, respectively; and measuring a normalized odor concentration N from the second resistive component and a value of a reference resistance corresponding to a reference odor concentration, in accordance with $$N = rns/rn$$

where rns is the value of said reference resistance.

6. A method as claimed in claim 5, further comprising judging the presence or absence of a fire by comparing the normalized odor concentration N with a given threshold value.

7. An odor concentration measurement apparatus comprising:

an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components;

a memory for storing values R, V, Em and Eo, where R is a value of said load resistance, V is a value of a voltage supplied from said power supply, Em a saturation level of the output of said odor sensor when the output is saturated, and Eo a base level of the output of said odor sensor when there is zero odor concentration; and a central processing unit for measuring the odor concentration by obtaining the value of said second resistive component from an output E of said odor sensor which is a voltage across said load resistance, in accordance with a prestored equation $$rn = R \cdot V(Em-E)(Em-Eo)Em^2(E-Eo)$$

where rn is the value of said second resistive component.

8. An odor concentration measurement apparatus comprising:

an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components;

a memory for storing values R, V, Em and Eo, where R is a value of said load resistance, V is a value of a voltage supplied from said power supply, Em a saturation level of the output of said odor sensor when the output is saturated, and Eo a base level of the output of said odor sensor when there is zero odor concentration; and a central processing un it for obtaining the value of said second resistive component from an output E of said odor sensor which is a voltage across said load resistance, in accordance with a prestored equation $$rn = R \cdot V(Em-E)(Em-Eo)/Em^2(E-Eo)$$

where rn is the value of said second resistive component;

wherein said central processing unit is further for measuring a normalized odor concentration N from the value of the second resistive component and a value of a reference resistance corresponding to a reference odor concentration, in accordance with another prestored equation $$N = rns/rn$$

where rns is the value of said reference resistance and is stored in said memory.

9. An apparatus as claimed in claim 8, wherein said central processing unit includes means for judging the presence or absence of a fire by comparing the normalized odor concentration with a prestored threshold value.

10. An apparatus as claimed in claim 8, further comprising:

a data base unit for storing first data indicative of a relation between a strength of a smoky smell and a smoldering stage of a fire, second data indicative of a relation between a size of a room and the smoky smell, and third data indicative of properties of an odor concentration diffusion; and judgment means for estimating a probability of an occurrence of a fire, based on said first, second and third data stored in a data base unit and the normalized odor concentration N, and for outputting a fire alarm signal when the estimated probability exceeds a given threshold.

11. An odor concentration measurement apparatus comprising:

an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components; and a memory for storing values Zm, Zo and Zn, where Zm, Zo and Zn are a value of the total resistance of said odor sensor when the output of said Odor sensor is saturated, a value of the total resistance when the output of said odor sensor is at a base level, and a value of the total resistance when the odor concentration is measured by said odor sensor, respectively; and a central processing unit for measuring the odor concentration by obtaining the value of said second resistive component from the total resistance of said odor sensor, in accordance with a prestored equation $$rn = (Zn-Zm)(Zo-Zm)/(Zo-Zn)$$

where rn is the value of the second resistive component.

12. An odor concentration measurement apparatus comprising:

an odor sensor connected across a power supply through a load resistance, wherein a total resistance of said odor sensor includes a parallel connection of a first resistive component having a value according to a surrounding environment including at least one of temperature and humidity and a second resistive component having a value according to an odor concentration, and a saturation resistive component connected in series with said parallel connection of said first and second resistive components; and a memory for storing values Zm, Zo and Zn, where Zm, Zo and Zn are a value of the total resistance of said odor sensor when the output of said odor sensor is saturated, a value of the total resistance when the output of said odor sensor is at a base level, and a value of the total resistance when the odor concentration is measured by said odor sensor, respectively; and a central processing unit for measuring the odor concentration by obtaining the value of said second resistive component from the total resistance of said odor sensor, in accordance with a prestored equation $$rn = (Zn-Zm)(Zo-Zm)/(Zo-Zn)$$

where rn is the value of the second resistive component; and wherein said central processing unit is further for measuring a normalized odor concentration N which is used to from the value of the second resistive component and a value of a reference resistance corresponding to a reference odor concentration, in accordance with another prestored equation $$N = rns/rn$$

where rns is the value of said reference resistance and is stored in said memory.

13. An apparatus as claimed in claim 12, wherein said central processing unit includes means for judging the presence or absence of a fire by comparing the normalized odor concentration with a prestored threshold value.

14. An apparatus as claimed in claim 12, further comprising:

a data base unit for storing first data indicative of a relation between a strength of a smoky smell and a smoldering stage of a fire, second data indicative of a relation between a size of a room and the smoky smell, and third data indicative of properties of an odor concentration diffusion; and judgment means for estimating a probability of an occurrence of a fire, based on said first, second and third data stored in a data base unit and the normalized odor concentration N, and for outputting a fire alarm signal when the estimated probability exceeds a given threshold.

* * * * *